(12) United States Patent
Dawidowski et al.

(10) Patent No.: US 6,646,169 B1
(45) Date of Patent: Nov. 11, 2003

(54) CONCENTRATED, STABLE ALKALI ALKOXIDE SOLUTIONS

(75) Inventors: Dirk Dawidowski, Frankfurt am Main (DE); Ute Emmel, Frankfurt am Main (DE); Wilfried Weiss, Oberursel (DE); Ulrich Wietelmann, Friedrichsdorf (DE)

(73) Assignee: Chemetall GmbH, Frankfurt Am Main (DE)

( * ) Notice: Subject to any disclaimer, the term of this patent is extended or adjusted under 35 U.S.C. 154(b) by 0 days.

(21) Appl. No.: 10/111,829

(22) PCT Filed: Nov. 8, 2000

(86) PCT No.: PCT/EP00/11027

§ 371 (c)(1),
(2), (4) Date: Jul. 10, 2002

(87) PCT Pub. No.: WO01/38277

PCT Pub. Date: May 31, 2001

(30) Foreign Application Priority Data

Nov. 24, 1999 (DE) .......................................... 199 56 558

(51) Int. Cl.$^7$ .............................................. C07C 31/30
(52) U.S. Cl. ........................................ 568/851; 568/579
(58) Field of Search ................................. 568/851, 579

(56) References Cited

U.S. PATENT DOCUMENTS

| 1,712,830 | A | * | 5/1929 | Kyrides ...................... 568/851 |
| 2,069,404 | A | * | 2/1937 | Cunningham ................ 568/835 |
| 2,796,443 | A | * | 6/1957 | Meyer et al. ................ 564/503 |
| 4,421,936 | A | * | 12/1983 | Smith et al. ................. 568/678 |
| H938 | H | * | 7/1991 | Paalman et al. ............. 544/263 |
| 6,150,569 | A | * | 11/2000 | Hamann et al. ............. 568/851 |
| 6,191,319 | B1 | * | 2/2001 | Hamann et al. ............. 568/851 |

* cited by examiner

Primary Examiner—Rosalynd Keys
(74) Attorney, Agent, or Firm—Fulbright & Jaworski L.L.P.

(57) ABSTRACT

Concentrated, stable solutions of alkali metal alkoxides ROM, which consist of an alkali metal cation and a secondary or tertiary alcohol residue, in aprotic solvents are described, wherein, relative to alkoxide content, the solutions contain at least 1.0 and at most 15 mol % of alkali metal hydroxide M'OH and at most 1.0 mol % of free alcohol R—OH, wherein R is a secondary or tertiary alkyl residue and wherein M and M' are mutually independently Li, Na, K, Rb or Cs. A process for the production of the solution and the use thereof are also described.

16 Claims, 1 Drawing Sheet

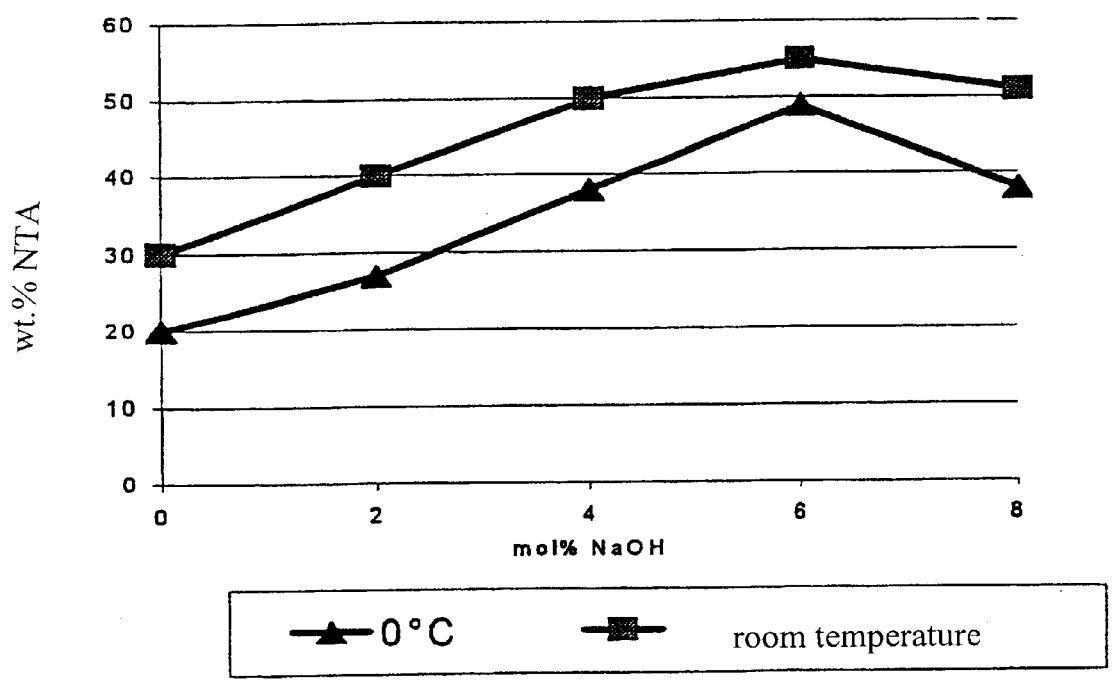
Fig. 1: Solubility of NTA in toluene as a function of NaOH content at 0°C and room temperature

CONCENTRATED, STABLE ALKALI ALKOXIDE SOLUTIONS

This invention relates to concentrated, stable solutions of alkali alkoxides of secondary and tertiary alcohols, to a process for the production thereof and to the use thereof.

Alkali metal alkoxides R—OM (R=alkyl having 3 to 20 C atoms, M=Li, Na, K, Rb, Cs) are compounds sensitive to hydrolysis which, by virtue of the basic properties thereof, are frequently used in organic synthesis. They are accordingly used as condensation, esterification and alkylation agents and for introducing the alkoxy group into other compounds (Williamson synthesis).

Alkali alkoxides are generals prepared by the action of alkali metals on alcohols in accordance with $$R\text{—}OH + M \rightarrow R\text{—}OM + \tfrac{1}{2}H_2\uparrow \qquad (1).$$

Apart from the elemental metal (M=Li, Na, K, Rb, Cs), it is also possible to use other reactive metal compounds ("metalation agents"), such as alkali metal hydrides, amides and organo-alkali metal compounds (for example butyllithium).

The reaction generally proceeds in the liquid phase, i.e. in the presence of a solvent. In the case of alkoxides of primary alcohols (for example methanol, ethanol, n-butanol), the solvent is preferably the primary alcohol itself. The alkoxides of secondary and tertiary alcohols are generally only sparingly soluble in alcohols. They are accordingly frequently produced in aprotic solvents (for example hydrocarbons, ethers).

After evaporation of the synthesis solutions, the alkoxides may be sold in the form of solid (pulverulous) products. The disadvantage of this commercial form is that, due to their basic properties, alkoxide dusts have a strongly corrosive action, i e. appropriate protective measures must be taken in order to prevent physical contact with the alkoxide powders. Liquid delivery forms, i. e. solutions, are particularly desired in order to avoid this handling-related disadvantage. Solutions are, however, only of economic interest if the alkoxide has good solubility, i. e. greater than 20%, over a wide temperature range.

The individual solubilities of alkoxides in a solvent are primarily determined by the metal M and the alkyl residue. In general, alkoxides derived from lithium are most readily soluble. Solubility is also a function of the volume and bulkiness of the alkyl group; the "larger" said group, the better is solubility in preferably slightly polar solvents (for example hydrocarbons).

However, in addition to these parameters influenced by the particular alcohol and metal, there are other factors which influence individual solubility. In the case of alkali alkoxides derived from secondary and tertiary alcohols, the residual alcohol content is one such factor.

It is known that alkoxides form complexes with free alcohols, which complexes are sparingly soluble in a polar or slightly polar solvents.

$$xR\text{—}OM + yR'\text{—}OH \rightarrow (R\text{—}OM)_x \cdot (R'\text{—}OH)_y \downarrow \qquad (2)$$

The presence of free alcohol in alkoxide solutions results either from incomplete reaction according to equation (1) or is a consequence of hydrolysis due to contact with air and/or water according to equation (3):

$$R\text{—}OM + H_2O \rightarrow R\text{—}OH + MOH \qquad (3)$$

The applicant's own investigations revealed that, for example in the case of concentrated sodium tert.-butylate solutions in methyl tert.-butyl ether (MTBE), tetrahydrofuran (THF) or toluene, the x'y stoichiometry of the sparingly soluble complex formed according to equation (2) is approx. 3–6:1, i. e. free alcohol is capable of removing a distinctly above stoichiometric quantity of alkoxide from the solution. The applicant's own investigations revealed that, for example in the case of concentrated sodium tert.-butylate solutions in methyl tert.-butyl ether (MTBE), tetrahydrofuran (THF) or toluene, the x:y stoichiometry of the sparingly soluble complex formed according to equation (2) is approx. 3–6:1, ie. free alcohol is capable of removing a distinctly superstoichiometric quantity of alkoxide from the solution.

From the above, it may be concluded that solutions of alkali alkoxides derived from secondary and tertiary alcohols should contain as little water and alcohol as possible in order to achieve maximum alkoxide solubilities.

The object of the present invention is to provide away of increasing the solubility of alkali metal alkoxides derived from secondary and tertiary alcohols and of reducing the susceptibility thereof to hydrolysing conditions, so improving the stability of these alkali metal alkoxide solutions.

The object is achieved by the solutions stated in claim 1, while claims 2 to 9 state variants of the solutions according to the invention. Claims 9 to 13 state a process for the production of the solutions according to the invention and claim 14 states a use of the solutions according to the invention.

The concept of the invention is to dissolve a mixture of an alkoxide ROM and an alkali metal hydroxide M'OH in an aprotic solvent, wherein R is a secondary or tertiary alkyl residue having 3 to 20 C atoms and wherein M and M' are mutually independently Li, Na, K, Rb or Cs.

Secondary or tertiary alcohols are, for example, isopropyl alcohol, sec.-butyl alcohol, tert.-butyl alcohol or tert.-amyl alcohol.

It has been found that a hydroxide content in the range between at least 0.5 and at most 15 mol % (preferred ranges are disclosed in the claims) in order to exert a distinctly favourable effect on the solubility of the alkali alkoxides. For applications in organic synthesis, such a hydroxide content is not generally disruptive because alkali hydroxides are less basic than alkoxides, ie. different reaction results should not generally be anticipated.

In order to prevent sparingly soluble alcohol/alkoxide complexes from precipitating out, the residual alcohol content should be as low as possible. The maximum residual free alcohol content of the solutions is at most 1.0 mol %, preferably at most 0.5 mol %.

Solvents which may be used are polar and/or non-polar aprotic solvents. It is possible to use aromatic hydrocarbons (for example toluene, benzene, xylene, ethylbenzene), or open-chain or cyclic aliphatic hydrocarbons (for example pentane, hexane, cyclohexane, heptane, octane) or ethers (open-chain or cyclic, mono- or polyfunctional, for example diethyl ether, tetrahydrofuran, 2-methyltetrahydrofuran, methyl tert.-butyl ether, 1,2-dimethoxyethane (1 ,2-DME), diethylene glycol dimethyl ether) or amides (for example dimethylformamide DMF) or dimethyl sulfoxide DMSO or acetals (for example diethoxymethane or diethoxyethane) or nitrites (for example acetonitrile). Mixtures of these substances may also be used.

There are various manners in which the alkali metal hydroxide may be incorporated: Isolated, pulverous alkoxides may be combined and mixed with an alkali metal hydroxide and then dissolved in an anhydrous, aprotic solvent. Should the hydroxide not be in finely divided form, the mixture would have to be ground. Since commercially available hydroxides are not completely anhydrous (they are markedly hygroscopic), it is often impossible to avoid entraining small quantities of water in this manner which have a negative impact on solubility. This may be counteracted by post-drying the solution (addition of M', M'H, molecular sieve, azeotropic removal of water).

It is simpler and more effective to incorporate the hydroxide during synthesis of the alkoxide. This is achieved, for example, by apportioning the calculated quantity of hydroxide (M'OH) or of water to the metalation agent (i.e. the alkali metal itself or the hydride, amide or an organoalkali metal compound). The solvents used are the above-mentioned polar and/or non-polar aprotic solvents. One particularly elegant variant also consists in adding, instead of completely anhydrous alcohol, a water/alcohol mixture prepared in the calculated ratio. When using water for in situ production of alkali metal hydroxide, an appropriate additional quantity of metalation agent must initially be introduced.

The person skilled in the art is aware of the various processing variants for alkoxide synthesis. It is, for example, also possible initially to introduce the alcohol and to apportion the metalation agent thereto. There are numerous conceivable variants as to how and when the water and metal hydroxide are incorporated.

In all cases, it is vital for both the alcohol and the water to be consumed as completely as possible in the reaction with the metalation agent. Consequently, depending upon the process variant, the metalation agent should preferably be used in excess (approx. 1 to 50%, preferably 1 to 10%).

It has been found that the presence of small quantities of water (0.5 to 10 mol %) generally has no significant effect upon the course of the formation reaction (i.e. rate of reaction, selectivity etc.). Accordingly, no further measures deviating from the prior art need be taken.

The alkoxide solutions according to the invention are used as reagents in organic synthesis.

The advantage of the secondary and tertiary alkoxide solutions according to the invention is the higher concentration of the solutions in comparison with the prior art, combined with the simultaneous stability of the solutions, which is advantageous in processing and economic terms.

The following Examples illustrate the subject matter of the invention in greater detail.

EXAMPLE 1

Solubilities of MO$^t$Bu

The solubilities of potassium and sodium tert.-butylate (MO$^t$Bu where M=K, Na) in toluene or methyl tert.-butyl ether (MTBE) with the addition of LiOH or NaOH (M'OH where M'=Li, Na) were investigated. To this end, the solubility of an alkoxide containing absolutely no residual base was initially determined in the solvent at a given temperature (several hours' stirring over a sediment of undissolved alkoxide and determination of alkalinity and residual base content by the Karl Fischer method). A specific quantity of an anhydrous, powdered alkali hydroxide was then added and stirring was again performed for several hours until an equilibrium was established.

TABLE 1

Solubilities of MO$^t$Bu

| Alkoxide | Alkali hydroxide M'OH | Conc. (mol %) | Solvent | Temperature (° C.) | Solubility (wt. %) |
|---|---|---|---|---|---|
| KO$^t$Bu | — | — | Toluene | 0 | 2.9 |
| KO$^t$Bu | NaOH | 5 | " | 0 | 4.2 |
| KO$^t$Bu | LiOH | 5 | " | 0 | 3.6 |
| KO$^t$Bu | — | — | " | 25 | 3.4 |
| KO$^t$Bu | NaOH | 5 | " | 25 | 4.5 |
| NaO$^t$Bu | — | — | " | 0 | 3.8 |
| NaO$^t$Bu | NaOH | 3 | " | 0 | 4.0 |
| NaO$^t$Bu | NaOH | 5 | " | 0 | 4.8 |
| NaO$^t$Bu | NaOH | 1.6 | MTBE | 25 | 23.4 |
| NaO$^t$Bu | NaOH | 3.0 | " | 25 | 27.7 |

As can be seen from Table 1, the solubility of potassium tert.-butylate (KOtBu) in toluene at 0° C. is increased by approx. 24% by the addition of 5 mol % LiOH and by approx. 45% by the addition of 5 mol % NaOH. A positive effect, albeit less marked, is also observed at 25° C.

The solubility of sodium tert.-butylate both in toluene at 0° C. and in MTBE at room temperature is also increased by addition of base.

Comparative Example A

Synthesis of Na tert.-amoxide (NTA) solution in toluene (without addition of M'OH)

103.3 g of sodium pieces (4.49 mol) were suspended in 600 g of toluene in a 2 litre jacketed reactor equipped with a reflux condenser and dropping funnel and, while being stirred, heated to the boiling point of toluene. Once the sodium had melted, the intensity of stirring was increased and 450 ml (4.09 mol) of tert.-amyl alcohol were added dropwise within 4 hours.

Once addition was complete, boiling was continued until evolution of gas had ceased completely (5 hours).

After cooling to approx. 50° C., the clear product solution was decanted off from the sodium residues, transferred into several Schlenk tubes and stored for several days at various temperatures. The total base content of the solutions was determined, on the basis of which the following maximum contents of dissolved Na tert.-amoxide (NTA content) were obtained:

| Temperature (° C.) | Total base content (mmol/g) | NTA content (%) |
|---|---|---|
| 34 | 3.577 | 39.5 |
| 21 | 3.275 | 36.1 |
| 0 | 2.298 | 25.3 |

EXAMPLE 2

Synthesis of NTA Solution in Toluene with Excess Na and Addition of 6 mol % H$_2$O 30 g of sodium (1.3 mol) were placed in 90 g of toluene and reacted at boiling point with a mixture of 82.9 g of t.-amyl alcohol (0.94 mol) and 1.08 g of water (60 mmol). After a post-reaction time of 3 hours, evolution of gas subsided completely. The decanted clear solution was transferred into two Schlenk tubes and stored for several days at 24° C. and 0° C. The total base and free base contents of the solutions were determined, on the basis of which the following NTA contents were obtained:

| Temperature (° C.) | Total base content (mmol/g) | Free base content[1] (mmol/g) | NTA content (%) |
|---|---|---|---|
| 24 | 5.14 | 0.31 | 53.2 |
| 0 | 4.80 | 0.30 | 49.6 |

[1]Karl Fischer titration

EXAMPLE 3

Synthesis of NTA Solution in Toluene, Addition of 5 mol % NaOH 27.6 g (1.2 mol) of sodium pieces and 2.0 g (50 mmol) of NaOH pellets were suspended in 90 g of toluene and combined at boiling temperature with 88.2 g of t.-amyl alcohol (1 mol). At the end oft he two-hour post-reaction phase, some of the NaOH pellets were still undissolved.

The decanted solution was stored at two different temperatures and the following NTA contents were obtained:

| Temperature (° C.) | Total base content (mmol/g) | Free base content[1] (mmol/g) | NTA content (%) |
|---|---|---|---|
| 23 | 4.40 | 0.165 | 46.6 |
| 0 | 3.94 | 0.185 | 41.3 |

[1]Karl Fischer titration

Analysis revealed in this case that only approx. 70% of the introduced quantity of NaOH had passed into solution, i. e. the actual rate of addition of NaOH was only 3.5 mol %.

The NTA solutions according to the invention from Examples 2 and 3 exhibit distinctly greater NTA solubility than does the NTA solution from Comparative Example A.

What is claimed is:

1. A solution of an alkali alkoxide of the formula ROM comprising
    an alkali metal cation and a secondary or tertiary alcohol residue in an aprotic solvent, wherein relative to alkoxide content, the solution contains at least 1.0 to not greater than 15 mol % of alkali metal hydroxide M'OH and not greater than 1.0 mol % of free alcohol R—OH, wherein R is a secondary or tertiary alkyl residue having 3 to 20° C. atoms and wherein M and M' are a metal independently selected from the group consisting of Li, Na, K, Rb and Cs.

2. A solution according to claim 1, wherein the content of alkali metal hydroxide M'OH is at least 1.5 mol %.

3. A solution according to claim 1, wherein the content of alkali metal hydroxide M'OH is not more than 12 mol%.

4. A solution according to claim 1, wherein the content of alkali metal hydroxide M'OH is at most 10 mol %.

5. A solution according to claim 1, wherein the content of alkali metal hydroxide M'OH is at most 8 mol %.

6. A solution according to claim 1, wherein the solution contains not greater than 0.5 mol % of free alcohol R—OH.

7. A process for the production of an alkoxide solution containing alkali metal hydroxide stated in claim 1, wherein an anhydrous mixture of a secondary or tertiary alkali alkoxide ROM and alkali metal hydroxide M'OH is dissolved in an anhydrous, aprotic solvent; wherein relative to alkoxide content, the solution contains at least 1.0 to not greater than 15 mol % of alkali metal hydroxide M'OH and not greater than 1.0 mol % of free alcohol R—OH, wherein R is a secondary or tertiary alkyl residue having 3 to 20° C. atoms and wherein M and M' are a metal independently selected from the group consisting of Li, Na, K, Rb and Cs.

8. A process for the production of an alkoxide solution containing alkali metal hydroxide comprising dissolving a mixture of at least one of a secondary or tertiary alkali alkoxide of formula ROM and an alkali metal hydroxide M'OH in an aprotic solvent and post-drying the solution, wherein relative to alkoxide content, the solution contains at least 1.0 to not greater than 15 mol % of alkali metal hydroxide M'OH and not greater than 1.0 mol % of free alcohol R—OH, wherein R is a secondary or tertiary alkyl residue having 3 to 20° C. atoms and wherein M and M' are a metal independently selected from the group consisting of Li, Na, K, Rb and Cs.

9. A process for the production of an alkoxide solution of an alkali alkoxide of formula ROM comprising reacting a mixture comprising at least one of water and alkali metal hydroxide, a secondary or tertiary alcohol and an aprotic solvent with a metalation agent, wherein the metalation agent is selected from the group consisting of an alkali metal, an alkali metal hydride, an alkali metal amide and an organoalkali metal compound, wherein relative to alkoxide content, the solution contains at least 1.0 to not greater than 15 mol % of alkali metal hydroxide M'OH and not greater than 1.0 mol % of free alcohol R—OH, wherein R is a secondary or tertiary alkyl residue having 3 to 20° C. atoms and wherein M and M' are a metal independently selected from the group consisting of Li, Na, K, Rb and Cs.

10. The process according to claim 9, wherein said metalation agent is an organoalkali metal compound.

11. The process according to claim 10, wherein said organoalkali metal compound is n-butyllithium.

12. A method of synthesizing an organic compound comprising admixing the solution of claim 1 with at least one organic moieties and reacting to form an organic compound.

13. A solution according to claim 1, wherein said aprotic solvent comprises at least one solvent selected from the group consisting of a hydrocarbon, an ether, an amide, an acetal, and a nitrile.

14. A solution according to claim 1, wherein said aprotic solvent comprises at least one solvent selected from the group consisting of an aromatic hydrocarbon, an open-chain hydrocarbon, a cyclic aliphatic hydrocarbon, an open-chain ether, a cyclic ether , mono-ether, a polyfunctional ether, an amide, an acetal, and a nitrile.

15. A solution according to claim 1, wherein M is Na and R is tert.-amyl $C(CH_3)_2C_2H_5$, the aprotic solvent is toluene and the concentration of Na-tert-amoxide amounts to 41.3 to 53.2 wt. %.

16. A solution according to claim 1, wherein M is Na and R is tert.-butyl $C(CH_3)_3$, the aprotic solvent is methyl tert.-butyl ether and the concentration of Na tert.-butoxide is at least 23.4 to 2.77 wt. %.

* * * * *